(12) United States Patent
Lipman

(10) Patent No.: US 6,326,421 B1
(45) Date of Patent: Dec. 4, 2001

(54) HYDROCOLLOID PRESSURE SENSITIVE ADHESIVES

(75) Inventor: Roger D. A. Lipman, Brasschaat (BE)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 09/508,621

(22) PCT Filed: Sep. 16, 1998

(86) PCT No.: PCT/GB98/02809

§ 371 Date: Jun. 5, 2000

§ 102(e) Date: Jun. 5, 2000

(87) PCT Pub. No.: WO99/14282

PCT Pub. Date: Mar. 25, 1999

(30) Foreign Application Priority Data

Sep. 16, 1997 (GB) .................................................. 9719711

(51) Int. Cl.⁷ ............................ C09J 153/00; A61L 15/06
(52) U.S. Cl. ............................... 524/22; 524/27; 524/45; 524/54; 524/55; 524/71; 524/274; 524/419; 523/111; 523/118; 428/355 BL; 428/356; 604/344
(58) Field of Search ..................... 428/355, 355 BL, 428/355 R, 356; 604/344; 524/22, 27, 45, 54, 55, 71, 274, 419; 523/111, 118

(56) References Cited

U.S. PATENT DOCUMENTS

| | | | |
|---|---|---|---|
| 3,339,546 | 9/1967 | Chen | 128/156 |
| 3,972,328 | 8/1976 | Chen | 128/156 |
| 4,166,051 | 8/1979 | Cilento et al. | 260/17.4 |
| 4,192,785 | 3/1980 | Chen et al. | 260/17.4 |
| 4,204,540 | 5/1980 | Cilento et al. | 128/283 |
| 4,231,369 | 11/1980 | Sørensen et al. | 128/283 |
| 4,253,460 | 3/1981 | Chen et al. | 128/283 |
| 4,367,732 | 1/1983 | Poulsen et al. | 128/156 |
| 4,378,018 | 3/1983 | Alexander et al. | 128/295 |
| 4,393,080 * | 7/1983 | Pawelchak et al. | 428/355 |
| 4,427,737 | 1/1984 | Cilento et al. | 428/315.7 |
| 4,477,325 | 10/1984 | Osburn | 204/159.12 |
| 4,496,357 | 1/1985 | Osburn | 604/336 |
| 4,505,976 | 3/1985 | Doehnert et al. | 428/355 |
| 4,538,603 | 9/1985 | Pawelchak et al. | 128/156 |
| 4,551,489 | 11/1985 | Bayha | 523/501 |
| 4,551,490 | 11/1985 | Doyle et al. | 524/22 |
| 4,598,004 | 7/1986 | Heinecke | 428/40 |
| 4,693,858 | 9/1987 | Volke | 264/101 |
| 4,738,257 | 4/1988 | Meyer et al. | 128/156 |
| 4,759,354 | 7/1988 | Quarfoot | 128/156 |
| 4,768,503 | 9/1988 | Highgate et al. | 128/156 |
| 4,952,618 | 8/1990 | Olsen | 524/17 |
| 5,006,401 | 4/1991 | Frank | 428/231 |
| 5,059,189 | 10/1991 | Cilento et al. | 604/307 |
| 5,133,821 | 7/1992 | Jensen | 156/245 |
| 5,270,358 | 12/1993 | Asmus | 524/55 |
| 5,274,036 * | 12/1993 | Korpman et al. | 525/92 |
| 5,322,876 | 6/1994 | Sasaki et al. | 524/366 |
| 5,429,591 | 7/1995 | Yamamoto et al. | 602/54 |
| 5,466,724 | 11/1995 | Volke et al. | 523/111 |
| 5,492,943 | 2/1996 | Stempel | 523/111 |
| 5,503,847 | 4/1996 | Queen et al. | 424/488 |
| 5,534,561 | 7/1996 | Volke | 523/111 |
| 5,545,154 | 8/1996 | Oberholtzer | 604/336 |
| 5,554,106 | 9/1996 | Layman-Spillar et al. | 602/42 |
| 5,569,207 | 10/1996 | Gisselberg et al. | 604/175 |
| 5,571,080 | 11/1996 | Jensen | 602/56 |
| 5,591,447 | 1/1997 | Jensen | 424/443 |
| 5,622,711 | 4/1997 | Chen | 424/445 |
| 5,633,010 | 5/1997 | Chen | 424/448 |
| 5,662,924 | 9/1997 | Rhodes | 424/445 |
| 5,674,578 | 10/1997 | Giori | 428/35.4 |

FOREIGN PATENT DOCUMENTS

| | | |
|---|---|---|
| 42 07 657 A1 | 9/1992 | (DE) . |
| 0 122 344 A1 | 10/1984 | (EP) . |
| 0 264 299 B1 | 4/1988 | (EP) . |
| 0 272 149 B1 | 6/1988 | (EP) . |
| 0 297 769 B1 | 1/1989 | (EP) . |
| 0 344 913 A1 | 12/1989 | (EP) . |
| 0 730 874 A2 | 9/1996 | (EP) . |
| 1088992 | 10/1967 | (GB) . |
| 1576522 | 10/1980 | (GB) . |
| 2 089 351 A | 6/1982 | (GB) . |
| 2 198 441 A | 6/1988 | (GB) . |
| WO 91/13935 | 9/1991 | (WO) . |
| WO 95/17166 | 6/1995 | (WO) . |
| WO 98/01167 | 1/1998 | (WO) . |

* cited by examiner

*Primary Examiner*—Daniel Zirker
(74) *Attorney, Agent, or Firm*—Christie, Parker & Hale, LLP

(57) ABSTRACT

A pressure-sensitive adhesive material made of a weakly elastic mixture comprising a continuous phase formed essentially from a physically cross-linked solid rubber, which comprises a blend of A-B-A block copolymer, such as a styrene-isoprene-styrene block copolymer and a diblock copolymer such as styrene-butadiene, styrene-isoprene or a hydrogenated styrene-diene copolymer such as styrenel/ ethylene butylene, a compatible tackifying resin and a low-molecular weight polyisobutylene, optionally modified by butyl rubber, and a discontinuous phase comprising one or more hydrocolloids that are soluble and/or swellable in water.

18 Claims, No Drawings

HYDROCOLLOID PRESSURE SENSITIVE ADHESIVES

This invention relates to a pressure sensitive adhesive material made of a weakly elastic mixture of the type comprising a continuous phase formed essentially from a physically cross-linked solid rubber such as a styrene-olefin-styrene block copolymer, for example a styrene-isoprene-styrene block copolymer, and a compatible tackifying resin, and a discontinuous phase comprising one or more hydrocolloids that are soluble and/or swellable in water. Small quantities of additives such as stabilisers and fumed silica may be present. The adhesive layer can be combined with a non-adhesive, water impervious film and can be used in wound care, ostomy care and in other medical products.

Pressure sensitive adhesive materials are used in many medical device fields and are made into products such as tapes, bandages, surgical drapes, IV dressings and the like. Hydrocolloid adhesives are a unique kind of medically useful pressure sensitive adhesive. Hydrocolloid adhesives have a duality of attributes in that they are inherently adhesive and inherently absorbent. They are useful as wound dressings because they can be applied directly to open wounds and can be secured on the surrounding intact skin, and as skin barriers because they protect the peristomal skin of ostomy patients. Particularly in the area of wound dressings, the known hydrocolloid adhesives have some limitations, because the absorption capacity of hydrocolloid dressings is normally insufficient to handle the large amount of exudate from certain especially chronic wounds. Also, hydrocolloid compositions are normally not very flexible or conformable, so that adhesion to movable body parts is difficult. The present invention overcomes some of the problems of the prior art, and extends the utility of hydrocolloid adhesives.

One aspect of the present invention relates to skin barriers and wound dressings comprising a layer of hydrocolloid adhesive coated on a non-adhesive, waterproof film. The skin barrier is used in a number of ways. One of these is for bandaging purposes, especially on movable body parts such as joints or on curved surfaces of the body. Another important use is for the protection of the skin around body openings, especially around the surgically created openings known as colostomies, ileostomies and urostomies.

Many hydrocolloid skin barriers are known and are used for these purposes. It is convenient to divide these into "integrated" compositions and "non-integrated" compositions. In this context, "integrated" means those compositions which do substantially retain their dimensional stability and form which saturated with wound exudate and/or other body fluid. "Non-integrated" means those compositions which become soft gels and amorphous as they become saturated with fluid. Some of the relevant prior art is summarised below.

Non-integrated Compositions

The first hydrocolloid compositions to be described were non-integrated. U.S. Pat. No. 3,339,546 discloses compositions which are inelastic, and which are non-integrated, i.e. which do not maintain their dimensional stability and become amorphous when imbibed with wound fluid or other body fluid. A typical formulation taught by this prior art is the composition formed from low molecular weight polyisobutylene (40% by wt.), pectin (20% by wt.), sodium carboxymethyl cellulose (20% by wt.) and gelatin (20% by wt.). This formulation is believed to be the basis of commercially successful skin barrier and wound care products. Such compositions form a soft gel when in contact with an exuding wound, and the resultant gel remains in the wound when the dressing is removed. This lack of integrity is a drawback. The remaining gel must be irrigated from the wound by the nurse who is performing the change of dressing, and this is both time consuming for the nurse and painful for the patient. Notwithstanding the drawbacks of this prior art bandage, however, the compositions taught by U.S. Pat. No. 3,339,546 are extremely gentle to the skin. This is thought to be due to a number of factors. First, the compositions of this patent contain a relatively small number of components. On a statistical basis therefore, fewer skin reactions can be expected. Second, the ingredients are usually food components or additives, and have a long history of use. Third, polyisobutylene contains a chemically saturated aliphatic carbon-carbon backbone, and therefore needs no stabiliser to reduce the degradation often seen in rubbery materials having chemical unsaturation in the backbone. Fourth, the compositions apparently maintain the skin moisture at an optimum level, by absorbing excess perspiration and reducing the amount of skin maceration that is normally associated with the wearing of a wound dressing for several days. Skin maceration leads to a reduction in the mechanical strength of the skin, and in turn leads, on removal of the bandage, to increased skin damage to the healthy skin surrounding the margin of the wound. This is often termed "mechanical irritation".

Integrated Compositions

The lack of integrity was a serious drawback in the use of these dressings and barriers and much development was completed in efforts to overcome the deficiency. Thus, GB-A-1,576,522, corresponding to U.S. Pat. No. 4,231,369, describes improved hydrocolloid compositions that are integrated. There is provided a sealing material for ostomy use consisting of a hydrocolloid dispersed in a continuous phase of styrene-isoprene-styrene copolymer, or other thermoplastic elastomer such as an ethylene-propylene copolymer. Also present is a hydrocarbon tackifier and optionally an oil extender and an antioxidant. This material is said to have the advantage of being elastomeric and flexible, and thus bandages made from it should adhere well to the skin and be conformable. Because of the styrene-isoprene-styrene block copolymer the composition is integrated. The styrene-isoprene-styrene block copolymer forms physical cross links within the continuous phase at room temperature. This is because the polystyrene segments within the copolymer are incompatible with the polyisoprene segments, and they associate at room temperature to glassy domains which act as the physical cross links to form a three dimensional lattice. However, because of the larger number of components, and in particular the tackifying resin and stabilisers, the material does tend to experience more complaints with irritation than does the material from U.S. Pat. No. 3,339,546. Also, because the hydrocolloid absorbent components in GB-A-1,576,522 are normally at a lower concentration in the final formulation than are the hydrocolloid components in U.S. Pat. No. 3,339,546, a lower absorption level is obtained. The absorption rate is also slower, because the integrated nature of the composition makes that lower level of chemical hydrocolloid components even more slowly accessible to the body fluid.

Both U.S. Pat. No. 4,477,325 and U.S. Pat. No. 4,738,257 recognise the shortcomings of barriers and dressings based upon formulae such as described in U.S. Pat. No. 3,339,546. These two later patents disclose barriers and dressings based on an integrated formulation containing a continuous phase composed of a blend of high vinyl acetate EVA copolymer (51% wt VA and 49% wt ethylene) and low molecular weight polyisobutylene, in which is dispersed a discontinuous phase containing a blend of a superabsorbent material, pectin and sodium carboxymethyl cellulose. The function of the EVA copolymer is to cross link in the presence of ionising radiation, such as gamma radiation at a dosage of, for example, 25 KGy, which would be used to sterilise dressings formed from the composition of the invention. The cross-linked network is formed essentially from the EVA polymer by irradiation of the EVA containing elastomeric phase. The problem with this type of system is that the dose from such a sterilisation process is widely variable in practice. A company offering services for the sterilisation of medical devices to a nominal dose of 25 KGy would typically specify a dose within the range of say 25–35 KGy, so that some dressings would receive close to the lower amount while some would receive the higher amount. It will readily be appreciated that such variation will lead to a variable cross link density within different dressings of even the same production batch, which in turn will lead to variable performance in terms of rate and capacity of fluid absorption.

U.S. Pat. No. 4,551,490 describes integrated hydrocolloid adhesives modified by diluting the amount of styrene-isoprene-styrene block copolymer adhesives present in the composition. The patent provides a medical grade pressure sensitive adhesive composition comprising a heterogeneous mixture of one or more polyisobutylenes or blends of polyisobutylenes and butyl rubber, one or more styrene radial or block copolymers, a tackifier, mineral oil and one or more water soluble and/or swellable hydrocolloid gums. It is believed that the polyisobutylenes, butyl rubber, mineral oil and tackifier serve to modify and plasticise predominantly the isoprene segment of the block/radial copolymer. In particular, the mineral oil is said to provide increased extensibility and aggressiveness of the adhesive. It is believed that the teachings of this patent form the basis of the commercially available hydrocolloid dressing products DuoDerm and Signa Dress. However, it has been found that the rates of absorption of saline with these compositions is very slow, and not very reproducible, and moreover very much less than the absorption levels available with the compositions of U.S. Pat. No. 3,339,546.

All the prior art cited above is believed to form the basis of commercially available hydrocolloid dressings and skin barriers. But in spite of the very considerable effort expended, it has heretofore not been possible to prepare an integrated hydrocolloid composition which has the absorption rate of a non-integrated composition. All the prior art discussed above discloses modifications to the continuous phase to achieve integrated compositions. The integrated continuous phase is achieved in each case only at the expense of one or other of the beneficial properties of the non-integrated composition described in U.S. Pat. No. 3,339,546.

The present invention consists in a pressure sensitive adhesive material essentially comprising:
1) a continuous phase formed from
    (a) a physically cross-linked solid rubber comprising a blend of linear or radial A-B-A block copolymers and not more than 85 % by weight of A-B block copolymer;
    (b) a compatible tackifying resin; and
    (c) a low-molecular weight polyisobutylene,
said continuous phase optionally being modified by up to 50% by weight of butyl rubber, and
2) a discontinuous phase comprising one or more hydrocolloids that are soluble and/or swellable in water.

We have surprisingly found that modification of the teachings of U.S. Pat. No. 4,551,490 allows the mineral oil component to be omitted and provides compositions that still have an integrated continuous phase but that are very much improved as far as their absorbent capacity is concerned. In one aspect the invention provides an adhesive skin barrier or a wound dressing comprising a non-adhesive, water impervious film carrying an adhesive layer formed of a weakly elastic mixture comprising a continuous phase formed from such a physically cross-linked solid rubber such as a styrene-isoprene-styrene block copolymer, a compatible tackifying resin and a low molecular weight polyisobutylene, and a discontinuous phase comprising one or more hydrocolloids that are soluble and/or swellable in water. Butyl rubber modifier may be present.

The pressure sensitive adhesives have the advantage over the prior art that they contain no materials known to irritate skin and mucous membranes, and they can be used in wound care, ostomy care and other medical products.

The A-B-A triblock component of the solid physically cross-linked thermoplastic elastomer may for example comprise styrene-olefin-styrene and/or styrene-alkane-styrene copolymers. The continuous phase provides "dry tack" to adhere the adhesive to dry, i.e. not moist, skin. Dispersed within the continuous phase is the discontinuous phase consisting substantially of hydrocolloid. The hydrocolloid functions as the absorbent, and to provide the "wet tack" that ensures the adhesive adheres to the skin and mucous membranes when they are moist. The hydrocolloid must be capable of swelling in water, and transporting water. The hydroclloids should preferably, though not necessarily, also be soluble in water. Suitable hydrocolloids include naturally derived products such as pectin, gelatin, starches, guar gum, gum arabic, locust bean gum, gum karaya, alginic acid and its sodium and/or calcium salts. Also useful are the synthetic hydrocolloids such as sodium carboxymethyl cellulose, cross-linked or crystalline sodium carboxymethyl cellulose, polyvinyl alcohol, polyvinyl pyrollidone, high molecular weight polyethylene glycols and polypropylene glycols.

The solid rubber component also includes simple A-B block copolymers. However, the proportion of A-B block copolymers, relative to the A-B-A block copolymers, should not normally exceed about 85 % by weight and lower amounts would normally be used. These block copolymers can be based on styrene-butadiene, styrene-isoprene,and hydrogenated styrene-diene copolymers such as styrene ethylene-butylene.

Suitable styrene-diene copolymers for the practice of the invention are exemplified by a blend of linear styrene-isoprene-styrene triblock copolymer and linear styrene-isoprene diblock copolymer. Such a material is available from Shell Chemical as Kraton D-1161 and has a bound styrene content of about 15% and a diblock content of 17%. A second example is a blend of linear styrene-isoprene-styrene triblock copolymer and linear styrene-isoprene diblock copolymer available from Shell Chemical as Kraton D-1117 and which has a bound styrene content of about 17% and a diblock content of 33%.

An example of a suitable hydrogenated styrene-diene copolymer is a thermoplastic elastomer comprising a blend of clear linear triblock and diblock copolymer based on styrene and ethylene-butylene, with a bound styrene of 14% mass. Such a material is commercially available from Shell Chemical Company, as Kraton G-1657. Another example is Kraton G-1652 from Shell Chemical Company which is a thermoplastic elastomer comprised of a clear linear triblock copolymer based on styrene and ethylene-butylene, S-E/B-

S, with a bound styrene content of about 30% by weight. Also suitable are polymers in which there is a combination of chemically saturated blocks and chemically unsaturated blocks. For example, a branched copolymer consisting of two polyisoprene chains attached to the rubber midblock of a styrene/ethylene-butylene/styrene triblock copolymer. Such a material is available from Shell Chemical Company as Kraton Research Product RP6919, with the trademark Tacky G. This material has a styrene content of 18%, and isoprene content of 36% and an ethylene-butylene content of 46% by weight. Also, a low styrene synthetic copolymer of butadiene and styrene, commonly called SBR rubber, can be used as a solid rubber.

The tackifier resin gives the necessary adhesion to the skin and is an integral component of the continuous phase. Any tackifying resin that is suitable for use with the elastomers specified above may in principle be employed in the invention.

Tackifying resins useful in the invention can be both naturally derived and synthetically produced. The resins derived from α and β pinene such as Piccolyte S-115, the pentaerythritol rosin esters such as Pentalyn H, and trimethylol propane rosin esters such as Staybelite Ester 10, are all useful in the invention. Also cyclopentadienyl resins such as Escorez 5300, and Adtac LV-E, a C5 synthetic hydrocarbon resin are useful tackifiers.

Within the continuous phase, the weight ratio of solid rubber to tackifier is about 1:0.5 to about 1:7, and is varied in order to obtain the desired degree of adhesiveness and tackiness. The low molecular weight polyisobutylene may be selected from one or more low molecular weight polyisobutylenes having a viscosity average molecular weight of from about 36,000 to about 70,000. Such polyisobutylenes are commercially available under the trademark Vistanex from Exxon Chemical as grades LMMS, LMMH and LMH, having viscosity average molecular weights of about 45,000 53,000 and 63,000 respectively. Optionally, an elastomeric polymer such as butyl rubber or a high molecular weight polyisobutylene may be blended into the continuous phase. The optional butyl rubber may be used in the viscosity average molecular weight range of about 200,000 to about 600,000 and is exemplified by the grades Butyl 065 or Butyl 077, both available from Exxon Chemical. The optional high molecular weight butyl rubber may be added in amount suitable to modify various properties of the final formulation, and may be from 0% to about 50% of the total weight of the continuous phase, typically 10 to 30 weight %. The addition of polymer stabilisers can be advantageous, to protect an unsaturated elastomer from degradation during processing. Suitable stabilisers useful in the practice of the invention include those normally indicated for use with styrene-olefin-styrene block copolymer thermoplastic elastomers such as organophosphites and the so-called hindered phenols, but any suitable stabiliser may be employed. An example of an organophosphite stabiliser is tris (nonylphenyl) phosphite, available as Polygard HR, manufactured by Uniroyal. Particularly useful are the hindered phenols, Irganox 1010 and Irganox 565, manufactured by Ciba. Irganox 1010 is a benzenepropanoic acid, 3,5 -bis(1, 1-dimethylethyl)-4-hydroxy-2,2-bis [[3- [3,5 -bis (1,1-dimethylethyl) -4-hydroxyphenol]-1-oxopropoxy]methyl]-1,3-propanediyl ester. Irganox 565 is phenol,4-[[4,6-bis (octylthio)-1,3,5 -triazine-2-yl]amino[-2,6-bis (1,1-dimethylethyl)-. Stabilizers may be used separately or in combination and suitable ranges are within 0.3–1.5% by weight based on the total formulation.

The stabilisers are always added to the continuous phase, as is shown in the examples.

The discontinuous phase comprises one or more hydrocolloids that are soluble and/or swellable in water. The water soluble hydrocolloids enable the final composition to adhere to moist body surfaces. This phenomenon is termed "wet tack". One or more water swellable hydrocolloids may also be present. Suitable water soluble hydrocolloids include synthetic hydrocolloids such as sodium carboxymethyl cellulose, and natural products such as gelatin, pectin, guar gum, locust bean gum, tragacanth gum, gum karaya, starches, gum arabic, alginic acid and its sodium and/or calcium salts. Other synthetic hydrocolloids such as polyvinyl alcohol, polyvinyl pyrollidone, high molecular weight polyethylene glycols and polypropylene glycols are useful. Optional water swellable hydrocolloids include cross-linked or crystalline sodium carboxymethyl cellulose, cross-linked dextran and starch-acrylonitrile graft copolymer. The amount of the water swellable hydrocolloid may be from 0–50% by weight of the discontinuous phase. The amount of discontinuous phase may be from about 15% to about 70% of the total weight of the adhesive, normally from about 20% to about 55% of the total adhesive by weight.

Useful as an additional optional additive is fumed silica. Fumed silica such as Aerosil 200 manufactured by Degussa can help in increasing the shear strength of the continuous phase. Some hydrocolloid adhesives have a propensity to cold flow. Cold flow is a measure of the viscous deformation of the adhesive under load which is manifested in the ability of the adhesive to squeeze out from under the backing or dressing. This is usually deleterious to dressing and barrier performance and the presence of silica can often improve cold flow performance.

Other components which may be added in minor amounts include pH controllers, bactericides, growth factors, wound healing components such as collagen and pigments such as $TiO_2$.

The adhesive compositions of the invention may be prepared as follows. The solid rubber for example a styrene-olefin-styrene copolymer and the tackifier component are blended together in a suitable mixer, normally a sigma blade mixer heated to about 170° C. About 1% phr of a suitable stabiliser, say Irganox 1010 available from Ciba-Geigy, can be added at this stage. Normally a small amount of the quantity of tackifier, say 20%, is added to the whole amount of the solid rubber and the tackifier is allowed to blend with the soft rubber. When all of the tackifier has been absorbed, another portion of the tackifier is added, say 30%, and the tackifier is absorbed into the styrene-olefin-styrene rubber. This is continued until all the tackifier is added, when a pourable tacky intermediate is obtained. The mixture is allowed to cool to about 130° C. and the butyl rubber or a high molecular weight polyisobutylene, if present, can be added, and blended in for a period of time. After further cooling to about 90° C., the low molecular weight polyisobutylene and the ingredients of the discontinuous phase can then be added. The water soluble gums, and/or other hydrocolloids, are added with continued mixing, and blended until fully mixed, normally for about 15–30 minutes. The fully mixed mass is then removed from the mixer, extruded or pressed to the desired thickness, and then laminated to suitable substrates.

EXAMPLE 1

The mixer was purged with nitrogen gas and heated to 160° C. The speed of the front, faster, blade was 47 rpm. The Kraton KD-1161N and the Irganox 1010 were charged to the Mixer at 160° C., and the mixer was started. After mixing for 5 minutes, the rubbery crumb coalesced, and the mixture of tackifying agents was added with continued mixing and nitrogen purging. After the tackifiers had completely mixed with the rubber, the mixer was cooled to 110° C. and the butyl rubber was added, together with sodium carboxymethyl cellulose. After complete mastication of the butyl rubber was achieved, the mixer was further cooled to 90° C. and the rest of the powders were added. The total time for this operation was about 90 minutes. The finished hydrocolloid was removed from the mixture with a spatula and pressed between two sheets of silicone release paper in a hydraulic press with the platens maintained at 90° C.

Example 2 was made in a similar way.

| Component | Description | Example 1 Ref 142A Amount in Mix, gm | Example 2 Ref 148C Amount in Mix, gm |
|---|---|---|---|
| Kraton D-1161NS | Styrene/isoprene/ styrene copolymer | 45.3 | 67.9 |
| Adtac LV-E | C5 hydrocarbon resin | 23.8 | 35.8 |
| Escorez 2203 LC | Rosin Ester | 50.0 | 75.0 |
| Vistanex LMMH | Low molecular weight polyisobutylene | 168 | — |
| Vistanex LMH | Low molecular weight polyisobutylene | — | 168 |
| Irganox 1010 | Stabiliser | .9 | 1.3 |
| Butyl Rubber | Modifier of continuous phase | 60 | — |
| Aerosil 200 | Modifier of continuous phase | 3 | — |
| Sodium CMC | Hydrocolloid absorbent | 84 | 84 |
| Pectin USP100 | Hydrocolloid absorbent | 84 | 84 |
| Aquasorb A-500 | Hydrocolloid absorbent | 84 | 84 |

Evaluation of Hydrocolloid Adhesives

| | Ex. 1 | Ex. 2 | B. Braun | Hartmann | H605 |
|---|---|---|---|---|---|
| Reverse tack, N/in | 30.3 | 29.9 | 12.9 | — | 28.7 |
| pa 90 SS N/in | 25.7 | 17.0 | 3.4 | — | 13 |
| Static shear, 0.5 kg, min | 78 | 238.5 | 417 | — | 322 |
| Thickness, mm | 1.7 | 1.56 | 0.9 | 1.2 | 1.8 |
| Static absorption, gm/m$^2$ after 24 hr. | 8198 | 7175 | 5103 | 3503 | 4623 |
| cold flow %, 10 kg | 19.6 | 5.7 | 4.9 | 14.4 | 11.7 |

The adhesives prepared in Examples 1 and 2 were compared with three commercially available products and the date shown in the above Table. The three commercial material are available from Brauns/SurgiTec, Hartmann and Salt-MediQuest (H605 ). The Hartmann product is a non-integrated hydrocolloid, and yet the absorption, as measured by the static absorption of 0.9% wt % saline solution after 24 hours, is inferior to the products of the instant invention. The Braun and H605 products show some integrated nature, but the absorption level is still far inferior to those of Examples 1 and 2.

What is claimed is:

1. A pressure sensitive adhesive material which is free of mineral oil and comprises:
   1) a continuous phase formed from
      (a) 10 to 30 wt % of a physically cross-linked solid rubber comprising a blend of linear or radial A-B-A block copolymers and 15 to 85% by weight, based on the total weight of component (a) of A-B block copolymer;
      (b) 18 to 40% of a compatible tackifying resin;
      (c) 20 to 60% of a low-molecular weight polyisobutylene; and
      (d) 0 to 50% by weight of butyl rubber modifier, and
   2) 15 to 70%, based on the total weight of the adhesive, of a discontinuous phase comprising one or more hydrocolloids that are soluble and/or swellable in water, all percentages being by weight and those of components (a) to (d) being based on the total weight of the continuous phase.

2. An adhesive material according to claim 1 wherein the A-B-A block copolymer component of the cross-linked solid rubber comprises a styrene-olefin-styrene or styrene-alkane-styrene block copolymer.

3. An adhesive material according to claim 1 or claim 2 wherein the cross-linked solid rubber comprises 15 to 50% by weight of A-B diblock copolymer.

4. An adhesive material according to claim 1 wherein the A-B block copolymer component ofthe solid rubber comprises a styrene-butadiene, styrene isoprene or hydrogenated styrene-diene copolymer.

5. An adhesive material according to claim 1 wherein the cross-linked solid rubber has a styrene content of 10 to 20% by weight.

6. An adhesive material according to claim 1 wherein the weight ratio of solid rubber to tackifying resin is from 1:0.5 to 1:7.

7. An adhesive material according to claim 1 wherein the low-molecular weight polyisobutylene has a viscosity average molecular weight of 36,000 to 70,000.

8. An adhesive material according to claim 1 wherein the modifying butyl rubber has a viscosity average molecular weight of 200,000 to 600,000.

9. An adhesive material according to claim 1 wherein the discontinuous phase comprises 20 to 55%, of the total weight of the adhesive.

10. An adhesive barrier or dressing for medical use comprising a non-adhesive, waterproof film having coated thereon a layer of a pressure-sensitive material according to claim 1.

11. An adhesive barrier or dressing according to claim 10 wherein the A-B-A block copolymer component of the cross-linked solid rubber comprises a block copolymer selected from styrene-olefin-styrene and styrene-alkane-styrene.

12. An adhesive barrier or dressing according to claim 10 wherein the cross-linked solid rubber comprises 15–50% by weight of A-B diblock copolymer.

13. An adhesive barrier or dressing according to claim 10 wherein the A-B block copolymer component of the solid rubber comprises a copolymer selected from styrene-butadiene, styrene-isoprene or hydrogenated styrene-diene copolymer.

14. An adhesive barrier or dressing according to claim 10 wherein the cross-linked solid rubber has a styrene content of 10–20% by weight.

15. An adhesive barrier or dressing according to claim 10 wherein the weight ratio of solid rubber to tackifying resin is from 1:0.5 to 1:7.

16. An adhesive barrier or dressing according to claim 10 wherein the low-molecular weight polyisobutylene has a viscosity average molecular weight of 36,000 to 70,000.

17. An adhesive barrier or dressing according to claim 10 wherein the modifying butyl rubber has a viscosity average molecular weight of 200,000 to 600,000.

18. An adhesive barrier or dressing according to claim 10 wherein the discontinuous phase comprises 20–55% of the total weight of the adhesive.

* * * * *